United States Patent [19]

Calamur et al.

[11] Patent Number: 5,254,781
[45] Date of Patent: Oct. 19, 1993

[54] OLEFINS PROCESS WHICH COMBINES HYDROCARBON CRACKING WITH COUPLING METHANE

[75] Inventors: Narasimhan Calamur, Willowbrook; George A. Huff, Jr., Naperville; Harold A. Lindahl, Riverside, all of Ill.

[73] Assignee: Amoco Corporation, Chicago, Ill.

[21] Appl. No.: 815,244

[22] Filed: Dec. 31, 1991

[51] Int. Cl.$^5$ .................................................. C07C 2/00
[52] U.S. Cl. .................................... 585/500; 585/943; 585/602; 585/910; 585/911
[58] Field of Search ............... 585/500, 943, 602, 910, 585/911

[56] References Cited

U.S. PATENT DOCUMENTS

| | | | |
|---|---|---|---|
| 3,223,746 | 12/1965 | Hammond et al. | 585/911 |
| 3,392,211 | 7/1968 | Buschmann et al. | 585/911 |
| 5,025,108 | 6/1991 | Cameron et al. | 585/500 |

Primary Examiner—Patrick P. Garvin
Assistant Examiner—E. D. Irzinski
Attorney, Agent, or Firm—Thomas E. Nemo; Wallace L. Oliver; Frank J. Sroka

[57] ABSTRACT

An olefins process is described which combines cracking of a hydrocarbon feedstock with the coupling of methane using an oxygen-affording gas such that the heat evolved in the exothermic methane coupling reaction is effectively transferred to the endothermic cracking process in a manner which does not allow the non-hydrocarbon products in the effluent of the methane coupling reaction to mix with the effluent of the cracking process. By combining the cryogenic requirements of the two processes, the refrigeration used in air liquifaction to separate oxygen for the methane coupling process can provide refrigerant nitrogen to liquify one or more of methane, ethylene and propylene which can be used in the cryogenic separation of the $C_2+$ hydrocarbon products in the cracking process effluent.

11 Claims, 4 Drawing Sheets

OLEFINS PROCESS WHICH COMBINES HYDROCARBON CRACKING WITH COUPLING METHANE

BACKGROUND OF THE INVENTION

This invention relates to a process for making olefins which combines the thermal and/or catalytic cracking of a hydrocarbon feedstock with the coupling of methane and allows separation of an enhanced amount of $C_2+$ products, and more particularly, to a process for making olefins in which a hydrocarbon feed is thermally cracked to form olefins in parallel with the catalytic coupling of methane to form largely $C_2$ hydrocarbons using an oxygen-affording gas, the methane coupling and cracking processes so arranged that the heat produced in the exothermic coupling reaction is effectively transferred to the endothermic cracking process, and in which the refrigeration required to liquify air to produce oxygen for the methane coupling process is used to effect the cryogenic separation of the products contained in the effluent from the cracking process.

The commercial production of olefins including importantly ethylene, propylene and smaller amounts of butadiene is generally accomplished by the thermal cracking using steam of ethane, propane or a hydrocarbon liquid ranging in boiling point from light straight-run gasoline through gas oil. In a typical ethylene plant the cracking furnaces represent about 25% of the cost of the unit while the compression, heating, dehydration, recovery and refrigeration sections represent the remaining about 75% of the total. This endothermic process is carried out in large pyrolysis furnaces with the expenditure of large quantities of heat which is provided in part by burning the methane produced in the cracking process. After cracking, the reactor effluent is put through a series of separation steps involving cryogenic separation of products such as ethylene and propylene. The total energy requirements for the process are thus very large and ways to reduce it are of substantial commercial interest. In addition, it is of interest to reduce the amount of methane produced in the cracking process, or to utilize it other than for its fuel value.

More recently, because of the supply side pressure to find non-petroleum sources for industrial chemicals and the environmental need to reduce methane flaring from producing oil wells, natural gas, a source which is relatively abundant in the United States and other locations elsewhere in the world, has been investigated as a source of hydrocarbons and oxygenates. Various methods to convert the methane in natural gas to hydrocarbons have been suggested and some commercialized. Projects in New Zealand and at Sasol in S. Africa are examples in which methane is converted to useful products. In New Zealand, methane is converted to methanol and then to hydrocarbons, and in Sasol, methane is first converted to syn gas and then to other products.

The direct conversion of methane to major industrial intermediates such as ethylene and propylene has been the subject of much research in the past 10 years. While a number of catalysts and processes have been suggested for the conversion none has yet been commercialized. One process which has been intensely researched is the high temperature methane coupling process using an oxygen-affording gas and a solid, metal oxide catalyst to form largely ethane and ethylene. Carbon dioxide formation which is favored thermodynamically is an undesired product in methane coupling as its formation uses carbon which is not readily available to form the desired hydrocarbons.

More recently in U.S. Pat. No. 5,025,108, Institut Francais du Petrole (IFP) has taught a process for producing olefins from natural gas which involves pre-separation of the $C_2+$ components from the methane, catalytic oxidation of the methane to primarily ethane and ethylene, and the return of the $C_2+$ components to the effluent side of of the methane coupling reaction where the saturated $C_2+$ components are then cracked to olefins. The process is said to effectively utilize the heat produced in the exothermic methane coupling to carry out the endothermic cracking process. The process has several drawbacks however including importantly the mixing of the carbon oxides and water components produced by the substantial amount of hydrocarbon burning in the methane coupling process into the cracking process stream. Such components require an expensive separation from the hydrocarbons downstream in the IFP process.

Now a way has been found to produce olefins in a process not having many of the past disincentives. The process integrates the production of the olefins by hydrocarbon cracking with the methane coupling in a manner in which the individual processes synergistically fit together. Realized objectives of the new process are:

1. Thermal integration of the endothermic olefin cracking process with the exothermic methane coupling process;
2. Thermal integration of the refrigeration processes for enriched or purified oxygen production, olefins recovery, and optionally, natural gas liquids processing;
3. High overall yield of olefins and other products with near complete feedstock utilization; and
4. Substantial reduction of $NO_x$ as a result of process heat being generated by the coupling of methane with oxygen rather than the combustion of fuel with air.

BRIEF DESCRIPTION OF THE INVENTION

The invention contained herein is directed to a process to make olefins which combines cracking of a hydrocarbon feedstock with the coupling of methane, said process comprising:

the coupling in a first zone of a first feed which is essentially methane using oxygen-affording gas to produce a product containing at least a significant amount of $C_2$ hydrocarbons;

hydrocarbon cracking in a second zone of a second feed which contains predominantly saturated hydrocarbons to form primarily an olefin-containing product;

effectively transferring heat evolved by said coupling from said first zone to said second zone to provide a majority of the heat required by said cracking without mixing the hot effluent of said coupling into said second zone;

combining the $C_2+$ containing portions of the effluents from said first zone and said second zone and individually separating the methane and ethylene and propylene components thereof; and returning unreacted methane contained in the effluent of said first zone together with methane contained in the effluent of said second zone to the feed of said first zone.

In another aspect, the invention contained herein is directed to a process to make olefins which combines cracking of a hydrocarbon feedstock with the coupling of methane, said process comprising:

the catalytic coupling in a first zone of a first feed which is essentially methane using oxygen to produce a product containing at least a significant amount of $C_2$ hydrocarbons;

hydrocarbon cracking in a second zone of a second feed which contains predominantly saturated hydrocarbons to form primarily an olefin-containing product; transferring heat evolved by said catalytic coupling from said first zone to said second zone to provide a majority of the heat required by said cracking without mixing the hot effluent of said catalytic coupling into said second zone;

combining the $C_2+$ containing portions of the effluents from said first zone and said second zone and separating the methane and at least the ethylene and propylene components thereof cryogenically using hydrocarbons and nitrogen; and returning unreacted methane contained in the effluent of said first zone together with methane contained in the effluent of said second zone to the feed of said first zone.

BRIEF DESCRIPTION OF THE DRAWING

FIG. 4 shows two embodiments of a combined process reactor in which heat transfer between the cracking and coupling processes can be maximized and the two reactions carried out separately.

DETAILED DESCRIPTION OF THE INVENTION

Figure 1:
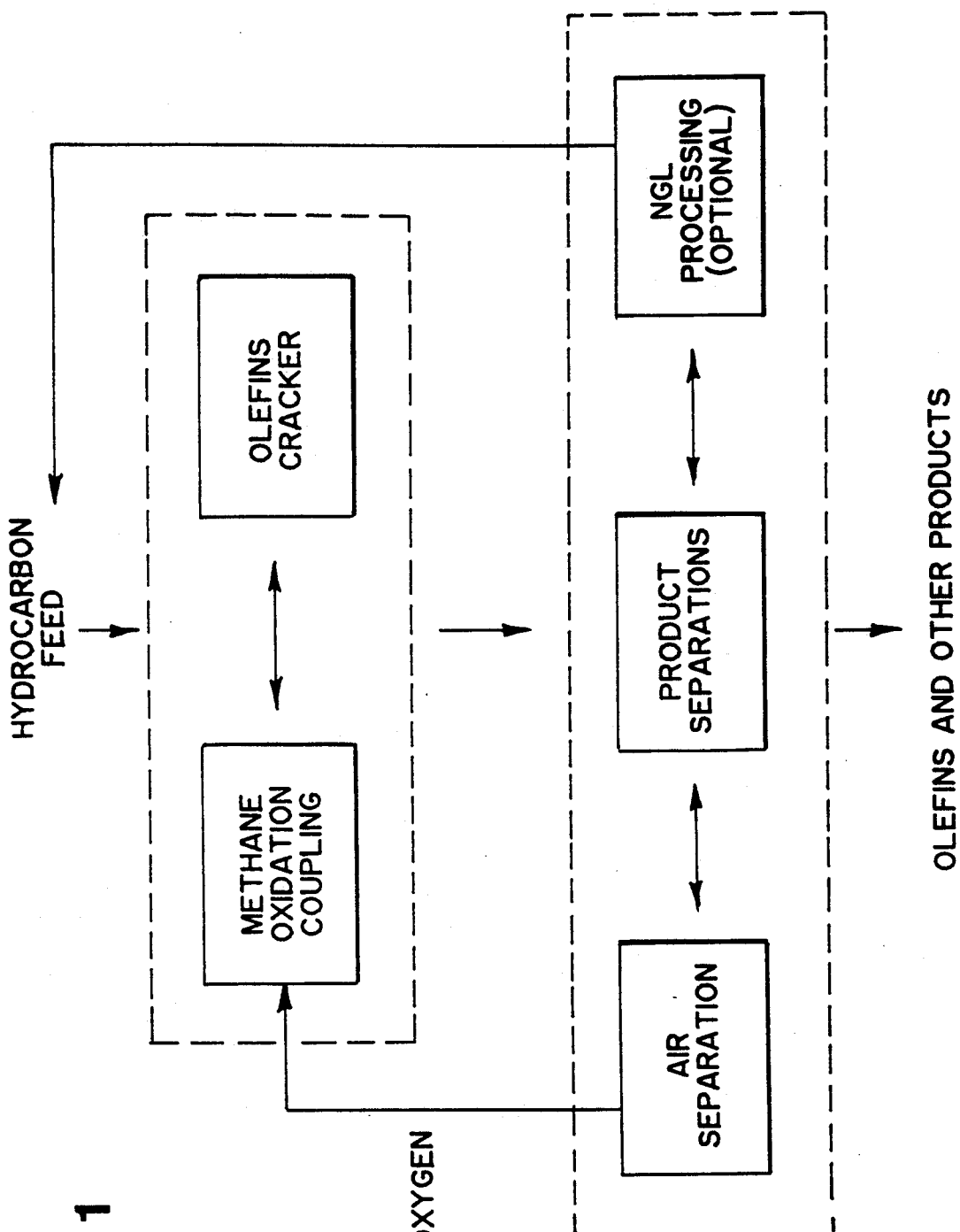
FIG. 1 shows an overall flow diagram for one embodiment of the olefins process.

The catalytic coupling of methane is carried out using a feed that is essentially methane which can be pure methane or methane containing various small amounts of other materials. The feed to the methane coupling reactor should not contain substantial amounts of $C_2+$ hydrocarbons as they are preferentially oxidatively dehydrogenated by the oxygen present in the coupling process at the expense of methane and also produce undesired water as a product. Natural gas containing $C_2+$ hydrocarbons can be used as a feed to the catalytic methane coupling unit after first separating the $C_2+$ hydrocarbons, for example, by first passing the natural gas through the demethanizer.

Although the methane coupling does not have to be carried out in the presence of a catalyst or agent, it is preferably to use one for the purpose of activating the methane. A large number of catalysts or agents are able to carry out methane coupling and a considerable number are recorded in the public literature. Catalysts or agents useful in the methane coupling reaction are generally heavy metal oxides, binary metal oxides and ternary metal oxides. Preferably, the metals used are those whose oxides are not volatile under the high temperature used in the methane coupling reaction. Metal oxides and metal oxide systems such as lead oxide, YBaZr oxide, SrLa oxide etc. may be used. It is preferable that the catalyst or agent used is one which has a high conversion and selectivity to $C_2$ hydrocarbons, particularly to ethylene, as can be understood by one skilled in the art.

Methane coupling is carried out over the catalyst or agent in the presence of an oxygen-affording gas such as air, oxygen-enriched air and oxygen, preferably oxygen, at pressures, temperatures and space velocities that are well known to those skilled in the art. Generally, the oxygen to methane ratio used is less than 1:1 so that the oxygen is completely converted in the coupling reaction and unreacted methane recycled to the methane coupling feed after separation of the methane coupling products. The product of methane coupling is largely the $C_2$ hydrocarbons, ethane and ethylene, with ethylene the most desired product. However, substantial amounts of carbon oxides and water as well as smaller amounts of $C_2+$ hydrocarbons can be formed as can be understood by one skilled in the art.

The type of reactor used can be a fixed bed, a moving bed, or a fluidized bed although a fixed bed reactor may be preferred from the point of view of economics. The partial oxidation catalyst or agent can be packed into the inside of tubes and distributed throughout the reactor space, but in a favored embodiment, the catalyst is adhered to the walls in the form of a skin on the reactor tube to facilitate transport of heat across the reactor wall. The exothermic methane coupling process and the endothermic hydrocarbon cracking process are carried out, desirably, in the same reactor separated by a thermally conducting wall between the reaction spaces. Preferably, a majority of the heat required in the endothermic cracking process is supplied by the heat evolved in the methane coupling process. More preferably, over 70% of the heat is supplied by methane coupling. The heat supplied by methane coupling is produced less pollutively than by burning, for example, methane with air as the amount of $NO_x$ is reduced to almost zero.

Figure 2:
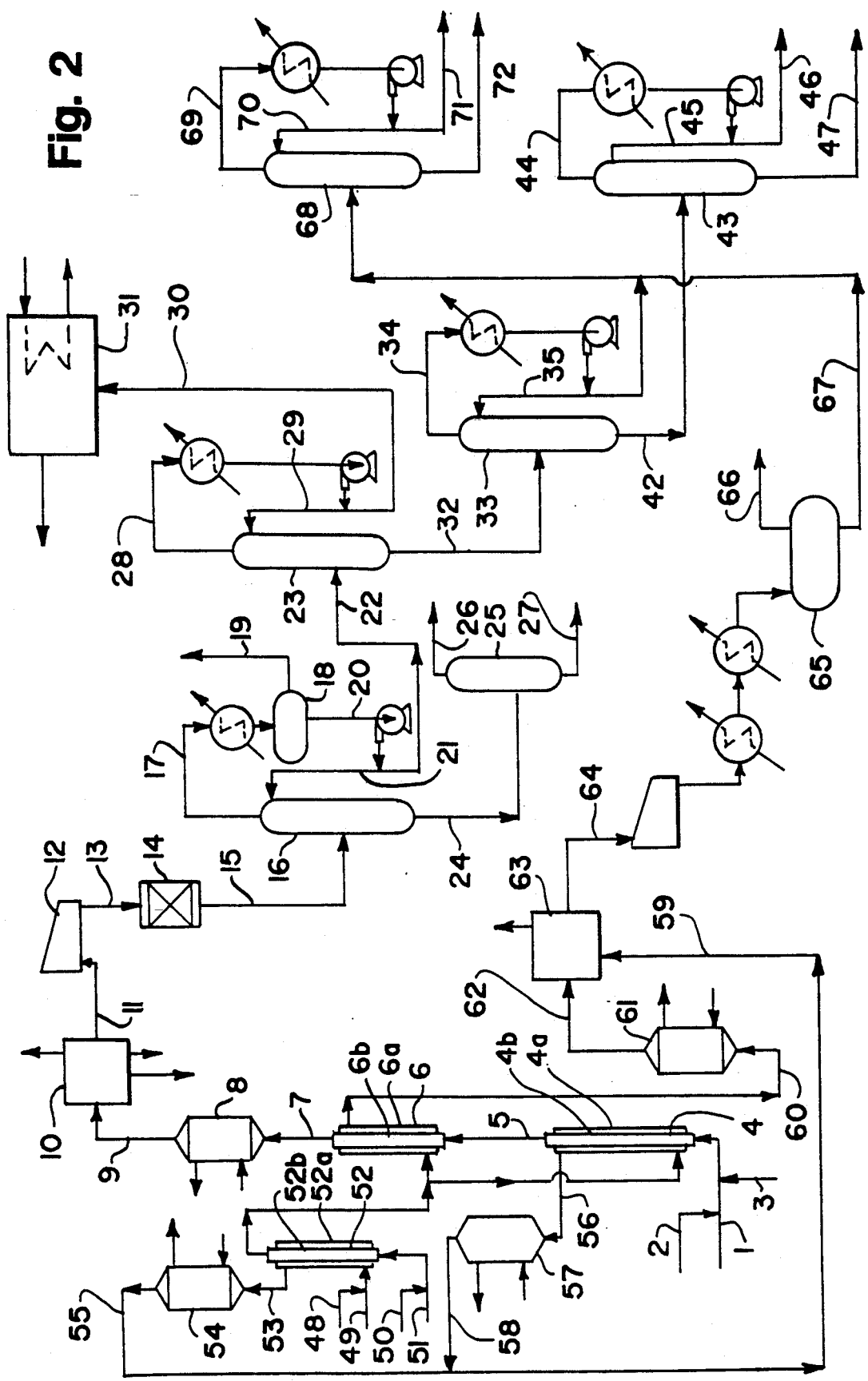
FIG. 2 is a more detailed flow diagram of one embodiment of the olefins process which uses propane as a feed to steam cracker.

In FIG. 2 which shows an embodiment of the combined olefins process using a largely propane feed, fresh propane through line 1 and recycle hydrocarbon through line 2 together with steam through line 3 enter preheater 4, which is a shell and tube methane coupling unit containing partial oxidation catalyst in space 4a. Propane is heated as it passes through inner tube 4b of unit 4 and flows out line 5 into the main methane coupling and thermal cracking unit 6. Coupling of the methane takes place in the catalyst-containing shell side of unit 6, space 6a, and thermal cracking of propane takes place in space 6b. If required, additional heat can be supplied to unit 6 to aid in hydrocarbon cracking. Cracked propane effluent flows from cracking furnace 6 through line 7 into heat exchanger 8 where boiler feed water is converted to high pressure steam. The effluent is then passed through line 9 into quench unit 10 where light products ($CO_2$ and $H_2S$) and heavy products (fuel oil and gasoline) are separated from the olefin fraction. The effluent from separator 10 which contains mainly $C_4$ and lower hydrocarbons is taken through line 11 to compressor 12, through line 13 and into acetylene hydrogenation unit 14. The hydrogenated product is then passed through line 15 into depropanizer 16. The $C_3$ and lighter fraction is taken off the depropanizer through line 17 and passed into separation drum 18 where hydrogen is removed through line 19 and the remainder returned to the top of depropanizer 16 through lines 20 and 21 and through line 22 to demethanizer 23. The $C_4+$ product from depropanizer 16 is passed through line 24 to debutanizer 25 where $C_4$s are removed at the top of the tower through line 26 and heavies such as gasoline through line 27. In demethanizer 23, methane is taken off the top of the tower through line 28, put through a heat exchanger and pumped through line 29 to the top of demethanizer tower 23 and to refrigeration recovery unit 31 through line 30. The heavier portion of the contents of demethanizer 23 (largely $C_2$ s and $C_3$ s) is passed through line 32 to deethanizer 33. In deethanizer 33, $C_2$ s and $C_3$ s are separated with $C_2$ s going out the top of column 33 through line 34 to a heat exchanger and pumped and back to the top of tower 33 through line 35 and sent through line 36 to $C_2$ splitter tower 68. Ethylene is taken off the top of column 68 and a portion returned to the top of the column and the remainder taken off as product through line 71. Ethane is taken off the bottom of column 68 through line 72 and recycled to line 2 or to an ethane cracking unit. $C_3$ s are taken off deethanizer 33 at the bottom through line 42 and sent to the $C_3$ splitter tower 43 where propylene is taken off overhead through line 44, cooled and pumped back to the top of tower 43 through line 45 and out to product recovery through line 46. Propane is taken off the bottom of tower 43 through line 47 and recycled to line 2.

Fresh methane and methane recycle from refrigeration recovery unit 31 are run through lines 48-51 into preheater 52 which is a shell and tube methane coupling reactor which contains partial oxidation catalyst in the shell side of preheater 52 in space 52a. Methane coupling occurs in space 52a and the methane coupling effluent from 52a exiting through line 53 goes through heat exchanger 54, and out line 55 where it is joined with methane coupling effluent from the shell side 4a of preheater 4 which exits preheater 4a through line 56 passing through heat exchanger 57 and then line 58 into line 59. The combined effluents are transferred through line 59 to amine treater 63 (along with methane coupling effluent from combined reactor 6 passing through line 60 into heat exchanger 61 and out line 62)where $CO_2$ is removed. In heat exchangers 54, 57 and 61, boiler feed water is converted to high pressure steam. After $CO_2$ removal, the methane coupling effluent passes through line 58 and is compressed and cooled and then lead to separation drum 65. Methane and carbon monoxide are removed through line 66 from separation drum 65 and may either be used as fuel or reformed to synthesis gas as the $CO/H_2$ ratio of the reformed product is close to ideal. The remainder of the methane coupling effluent(ideally nearly all $C_2$ s) is then fed to $C_2$ splitter tower 68 through line 67. Primarily ethylene is taken over head through line 69, cooled and split with one portion going back to the top of tower 68 through line 70 and part taken off as ethylene product through line 71. Ethane is taken off tower 68 through line 72 and returned to the process through recycle line 2 or to an ethane cracker.

Figure 3:
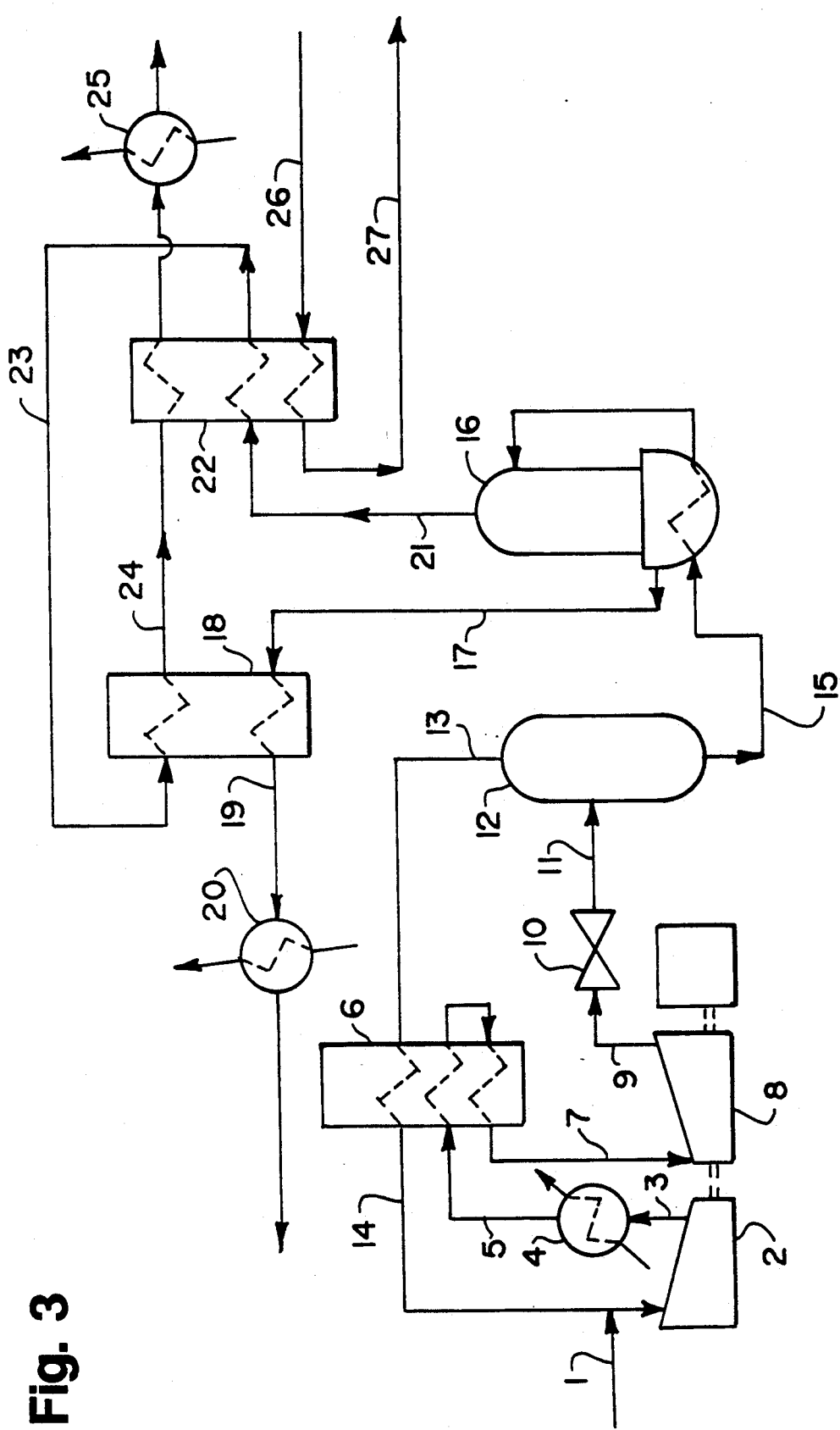
FIG. 3 shows a flow diagram for one embodiment of the combined refrigeration portion of the olefins process.
Figure 4B:
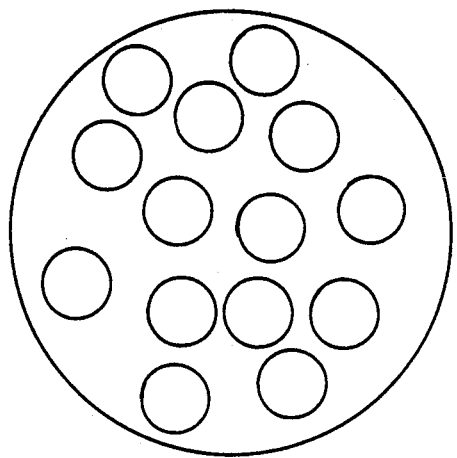
In FIG. 4b the cross section of a shell-and-tube reactor is shown in which hydrocarbon cracking takes place within the multiple tubes contained in the reactor and methane coupling takes place on the shell side of the tubes.
Figure 4A:
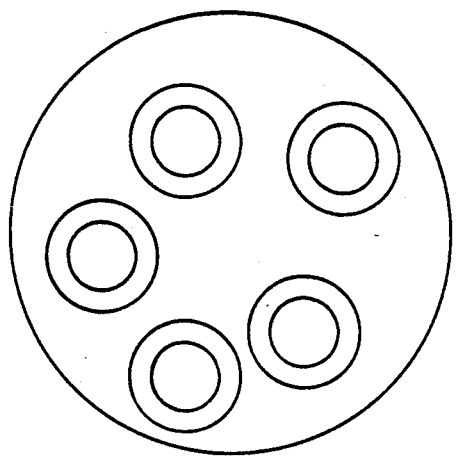
In FIG. 4a the cross section of a double-pipe-bundle reactor is shown in which catalytic coupling occurs in the catalyst-loaded annular space and hydrocarbon cracking occurs inside the center tube of each of the multiple double pipes and, optionally, also in the space between the shell sides of the pipes and the reactor wall.

In FIG. 3 which shows one embodiment of the combined refrigeration process for both the hydrocarbon cracking and methane coupling units, feed air enters through line 1 and is compressed in compressor 2, exiting at line 3 into heat exchanger 4 where it is cooled. The compressed air is sent to cold box 6 where it is further cooled and sent through line 7 to expander 8.

The cooled air from expander 8 is sent through line 9 to be further cooled by expansion through valve 10. The mixture of liquid and vapor air is then sent through line 11 to separator 12, where air vapor is returned to the compressor feed through line 14, first going through cold box 6 and line 13. The liquid air in separator 12 is transferred to still 16 through line 15 where the oxygen and nitrogen are separated by fractionation. The oxygen is taken off the bottom of still 16 through line 17, cold box 18 and put through line 19 to heat exchanger 20 from where it is sent to the methane coupling unit. Nitrogen vapor is taken off the top of still 16 through line 21 to cold box 22. It is then returned to cold box 18 through line 23 and sent back to cold box 22 through line 24 and then out through heat exchanger 25. Methane, ethylene and propylene from olefins production are cooled in cold box 22, entering through, for example, line 26 and then sent to the demethanizer, deethanizer and depropanizer sections of the olefins separation unit through, for example, line 27.

Instead of introducing feed air to the liquid air plant in FIG. 2 at ambient temperature, advantage can be taken of the existing refrigeration unit present in the usual olefins plant. In this embodiment, feed air is first cooled in stages in the propylene refrigeration unit and then further cooled in the ethylene refrigeration unit. It may be fed then to the liquid air plant at temperatures down to $-150°$ F. at 16 psia.

Hydrocarbon cracking is carried out using a feed which is ethane, propane or a hydrocarbon liquid ranging in boiling point from light straight-run gasoline through gas oil. Ethane, propane or mixtures thereof is the preferred feed to a hydrocarbon cracking unit. Generally, hydrocarbon cracking is carried out thermally in the presence of dilution steam in large cracking furnaces which are heated by burning at least in part methane and other waste gases from the olefins process resulting in large amounts of $NO_x$ pollutants. The hydrocarbon cracking process is very endothermic and requires large quantities of heat per pound of product. However, newer methods of processing hydrocarbons utilizes at least to some extent catalytic processes which are better able to be tuned to produce a particular product state. The amount of steam used per pound of feed in the thermal process depends to some extent on the feed used and the product slate desired. Generally, steam pressures are in the range of about 30 lbs per sq in to about 80 lbs per sq in, and amounts of steam used are in the range of about 0.2 lbs of steam per lb of feed to 0.7 lbs of steam per lb of feed. The temperature, pressure and space velocity ranges used in thermal hydrocarbon cracking processes to some extent depend upon the feed used and the product slate desired, which are well known as may be appreciated by one skilled in the art.

The type of furnace used in the thermal cracking process is also well known. However the ceramic honeycomb furnace which is described in U.S. Pat. No. 4,926,001, the contents of which patent are specifically incorporated herein by reference, is an example of a new type of cracking furnace which could have a special utility for this process.

The following Examples will serve to illustrate certain specific embodiments of the herein disclosed invention. These Examples should not, however, be construed as limiting the scope of the novel invention as there are many variations which may be made thereon without departing from the spirit of the disclosed invention, as those of skill in the art will recognize.

EXAMPLES

Example 1

Two similar feedstocks having the compositions set out below are cracked, one by a conventional thermal cracking process and one by the combined process of this invention involving the catalytic coupling of methane as represented by the embodiment in FIG. 2. The results are shown in Table 1 below. For the same amount of ethylene produced, the combined process consumes less feed, about the same amount of by-products and considerably less $CO_2$ and $NO_x$ pollutants.

TABLE 1

|  | Conventional Process | Combined Process |
|---|---|---|
|  | lbs/lb of ethylene produced | |
| Feedstock | | |
| Ethane | 0.40 | 0.34 |
| Propane | 0.52 | 0.44 |
| Naphtha | 1.52 | 1.28 |
| Methane | — | 0.20 |
| TOTAL FEED | 2.44 | 2.26 |
| Products | | |
| Hydrogen | 0.05 | 0.05 |
| Ethylene | 1.00 | 1.00 |
| Propylene | 0.33 | 0.29 |
| Butadiene | 0.10 | 0.09 |
| Butylenes | 0.07 | 0.07 |
| Pyrolysis Gasoline | 0.36 | 0.26 |
| Fuel Product | 0.53 ($H_2$, $CH_4$) | 0.50 ($CH_4$, CO) |
| TOTAL FEED | 2.44 | 2.26 |
| FUEL CONSUMED | 0.47 | 0.00 |
| Combustion Products | | |
| Carbon Dioxide | 1.29 | 0.09 pure |
| nitrogen | 4.03 | 0.76 pure |
| $NO_x$ | Substantial | very little |

TABLE 2

|  | Conventional Process | Combined Process |
|---|---|---|
|  | lbs/lb of ethylene produced | |
| Feedstock | | |
| Propane | 2.15 | 1.75 |
| Methane | — | 0.40 |
| TOTAL FEED | 2.15 | 2.15 |
| Products | | |
| Hydrogen | 0.05 | 0.04 |
| Ethylene | 1.00 | 1.00 |
| Propylene | 0.38 | 0.35 |
| Butadiene | 0.06 | 0.05 |
| Butylenes | 0.02 | 0.02 |
| Pyrolysis | 0.10 | 0.08 |
| Gasoline Fuel Product | 0.54 ($H_2$, $CH_4$) | 0.61 ($CH_4$, CO) |
| TOTAL FEED | 2.15 | 2.15 |
| FUEL CONSUMED | 0.40 | 0.00 |
| Combustion Products | | |
| Carbon Dioxide | 1.11 | 0.09 pure |
| Nitrogen | 3.47 | 1.54 pure |
| $NO_x$ | Substantial | little |

Example 2

Two similar feedstocks having the compositions set out below are cracked, one by a conventional thermal cracking process and one by the combined process of this invention involving the catalytic coupling of methane as represented by the embodiment in FIG. 2. The results are shown in Table 2 below. For the same amount of ethylene produced, the combined process consumes less propane, about the same amount of by-products and considerably less $CO_2$ and $NO_x$ pollutants.

Example 3

Referring to the embodiment set out in FIG. 1, a feed to the olefins process of between 645 MM lbs/yr of ethane and 835 MM lbs/yr of propane produces by thermal cracking about 1000 MM lbs/yr of ethylene, 235 MM lbs/yr of methane, and 600 MM lbs/yr of other products. The 235 MM lbs/yr of methane is combined with another 600 MM lbs/yr of methane from, for example, natural gas and fed together with 675 MM lbs/yr of oxygen from an air liquefaction plant using as a feed 3500 MM lbs/yr of air a partial oxidation unit from which 375 MM lbs/yr of fuel(CO and methane) is recovered and 150 MM lbs/yr of $C_2+$ products are made.

Example 4

Referring to the embodiment set out in FIG. 3, a feed of 420M lbs/hr of air is fed to the compressor and 98M lbs/hr of oxygen at 90° F. and 30 psi plus 322M lbs/hr of nitrogen at 90° F. and 30 psi are produced. The cooled nitrogen is able to produce 135, 65 and 200M lbs/hr of methane, ethylene and propylene at −270° F., −145° F. and −35° F. and 45, 20 and 155 psi respectively, to send to the demethanizer, deethanizer, and depropanizer sections of the hydrocarbon cracking process.

Example 5

In the embodiment set out in FIG. 3, feed air can be supplied to the air separation process at −150° F. instead of 90° F. as in Example 4 by passing the feed air first through, for example, three cooling stages of an existing propylene refrigeration unit where the air is successively cooled to 50° F., 5° F. and −25° F. The air is then further cooled by passing it through, for example, three cooling stages on the ethylene refrigeration unit where it is cooled successively to −60° F., −90° F. and −150° F.

What is claimed is:

1. A process to make olefins which combines cracking of a hydrocarbon feedstock with the coupling of methane, said process comprising:
    the coupling in a first zone of a first feed which is essentially methane using an oxygen-affording gas to produce a product containing $C_2$ hydrocarbons;
    hydrocarbon cracking in a second zone of a second feed which contains predominantly saturated hydrocarbons to form primarily an olefin-containing product;
    effectively transferring heat evolved by said coupling from said first zone to said second zone to provide a majority of the heat required by said cracking without mixing the hot effluent of said coupling into said second zone;
    combining the $C_2+$ containing portions of the effluents from said first zone and said second zone and individually separating the methane and at least the ethylene and propylene olefinic hydrocarbon components thereof; and
    returning unreacted methane contained in the effluent of said first zone together with methane contained in the effluent of said second zone to the feed to said first zone.

2. The process of claim 1 wherein said hydrocarbon feedstock is thermally cracked in the presence of steam, said coupling is catalytic, and wherein said separating the methane and at least the ethylene and propylene components thereof is carried out cryogenically using hydrocarbons and nitrogen as refrigerants.

3. The process of claim 2 wherein said oxygen-affording gas is essentially oxygen which is separated from air by liquifaction and where the nitrogen component of said air is used to liquify one or more of methane, ethylene and propylene, each under moderate pressure, to provide one or more cryogenic liquids used to effect the cryogenic separation of said olefinic hydrocarbon components.

4. The process of claim 1 wherein said coupling in said first zone is catalytic.

5. The process of claim 4 wherein said hydrocarbon feedstock is thermally cracked and wherein said separating the methane and at least the ethylene and propylene components thereof is carried out cryogenically using hydrocarbons and nitrogen as refrigerants.

6. The process of claim 5 wherein said oxygen-affording gas is essentially oxygen which is separated from air by liquification and where the nitrogen component of said air is used to liquify one or more of methane, ethylene and propylene, each under moderate pressure, to provide one or more cryogenic liquids used to effect the cryogenic separation of said olefinic hydrocarbon components.

7. The process of claim 3 wherein said catalytic coupling of methane reaction and said hydrocarbon cracking reaction are separated by a thermally conductive wall which is in good thermal contact with both of said reactions in a single vessel.

8. The process of claim 6 wherein said catalytic coupling of methane reaction and said hydrocarbon cracking reaction are separated by a thermally conductive wall which is in good thermal contact with both of said reactions in a single vessel.

9. The process of claim 1 wherein heat is transferred between said hydrocarbon cracking and said coupling reactions by transfer of a heated particulate solid between said first and said second zones.

10. The process of claim 3 wherein heat is transferred between said hydrocarbon cracking and said coupling reactions by transfer of a heated particulate solid between said first and said second zones.

11. The process of claim 4 wherein heat is transferred between said hydrocarbon cracking and said coupling reactions by transfer of a heated particulate solid between said first and said second zones.

* * * * *